United States Patent [19]

Okada

[11] Patent Number: 4,801,294
[45] Date of Patent: Jan. 31, 1989

[54] CATHETER FOR NASOGASTRIC INTUBATION

[75] Inventor: Yosuke Okada, Morimachi, Japan

[73] Assignee: Sherwood Medical Company, St. Louis, Mo.

[21] Appl. No.: 936,868

[22] Filed: Dec. 2, 1986

[30] Foreign Application Priority Data

Dec. 9, 1985 [JP] Japan .............. 60-189202[U]

[51] Int. Cl.⁴ .............................. A61M 25/00
[52] U.S. Cl. ........................ 604/171; 604/161; 604/280; 128/DIG. 26
[58] Field of Search .............. 604/158–172, 604/280, 54

[56] References Cited

U.S. PATENT DOCUMENTS

| 3,550,591 | 12/1970 | MacGregor | 604/161 |
| 4,114,626 | 9/1978 | Beran | 128/348 |
| 4,120,304 | 10/1978 | Moor | 128/348 |
| 4,175,564 | 11/1979 | Kwak | 604/54 X |
| 4,351,331 | 9/1982 | Gereg | 128/207.17 |
| 4,473,067 | 9/1984 | Schiff | 604/158 X |
| 4,596,559 | 6/1986 | Fleischhacker | 604/161 X |
| 4,631,059 | 12/1986 | Wolveh et al. | 604/280 |

FOREIGN PATENT DOCUMENTS 0021446 1/1981 European Pat. Off. .
60-222067 11/1985 Japan .

Primary Examiner—Dalton L. Truluck
Attorney, Agent, or Firm—Stanley N. Garber; Andrew J. Beck; William R. O'Meara

[57] ABSTRACT

The present invention provides a catheter for nasogastric intubation comprising a plastic sheath tube and a fixing means of said tube at nose, said tube having a longitudinal tear-off line over the full length thereof and having elasticity and rigidity slightly larger than those of said catheter, said catheter being inserted entirely in said plastic sheath tube slidably.

14 Claims, 2 Drawing Sheets

CATHETER FOR NASOGASTRIC INTUBATION

BACKGROUND OF THE INVENTION

1. Field of the Invention

This invention relates to a catheter for nasogastric intubation.

2. Description of the Prior Art

Normally, a catheter for nasogastric intubation for supplying nutrition comprises a weight portion in which the weight is sealed into a distal end of a soft small-diameter plastic tube. The tube is inserted from a nostril into the stomach or the intestines, making use of its weight, so as to supply nutrition through one or two side holes positioned slightly above the weight portion.

Since the catheter is kept placed through the nostril for a long period of time, a patient feels a considerable pain. To relieve this pain, it is preferable that the catheter be formed of a material as soft as possible. Further, since the catheter is kept in contact with the walls of the internal organs for a long period of time, if the catheter is formed of a hard material, the tissue of the walls of the internal organs may be damaged. For this reason, the catherter should be formed from a soft plastic tube. However, since the soft plastic tube lacks stiffness, it is difficult for the soft tube to be inserted since it must pass into the greatly bended stomach and intestines, through the oesophagus beyond the narrow-passage larynx, and through the nostril.

For this reason, in a conventional method, a guide wire is inserted into the inner cavity of the catheter to increase stiffness. However, in this method in which a guide wire is moved into the catheter, a lubricant has to be coated on the internal surface of the catheter to decrease the frictional resistance between the wire and catheter and in addition, insertion of the guide wire is cumbersome.

Furthermore, there is a danger that when inserting the guide wire, the end of the wire may project from the side holes of the catheter and pierce the walls of the internal organs.

SUMMARY AND OBJECT OF THE INVENTION

This invention has been achieved in an attempt of overcoming disadvantages as described above, and wherein a catheter is inserted and encased into a plastic sheath tube having a longitudinal tear-off line over the full length thereof and having elasticity and rigidity slightly higher than those of the catheter, thereby insertable into the stomach or the intestines. With this arrangement, the catheter can be easily inserted into the objectives including the nostril. After insertion, the sheath tube is removed by longitudinally tearing-off the sheath tube externally of the nostril with the catheter fixed to the fixing means on the nasogastric intubation tube. The sheath tube is raised with the result that only the catheter remains held within the stomach and intestines and without the catheter being raised together with the sheath tube because the catheter is fixed on the fixing means. Although the tearing-off of the sheath tube may be carried out easily because of the tube fixing means is secured externally of the nostril as shown in FIG. 5, in this invention, it can be more easily carried out.

The object of the present invention is to solve the above mentioned problems. It provides a catheter for nasogastric intubation that comprises a plastic sheath tube, a catheter body and a fixing means for positioning at the nose. The sheath tube has a longitudinal tear-off line over the full length thereof and has an elasticity and rigidity slightly higher than those of the catheter. The catheter is slidably insertable into the plastic sheath tube. The fixing means comprises a base plate with a rising portion integrally shaped and having an opening from which the splitted sheath tube can be pulled out in mutually opposite directions. The fixing means has a big passing hole which can softly or loosely hold the outer periphery of said catheter and a small passing hole which firmly pinches said catheter at a catheter pinch portion of the fixing means, while the big passing hole and the small passing hole are communicated by a connecting groove.

Since this invention has such a constitution as described above in the fixing means at the nose, when the sheath tube is pulled out, the splitted sheath tube is divided into two parts from the fixing means openings respectively and in opposite directions by passing through the rising portion from the bottom of the base plate. By moving the catheter body from the large hole to the small hole through the connected groove to fixedly pinch it and raising the sheath tube, said sheath tube can be easily separated from the catheter. Accordingly, the catheter body can remain easily in the stomach by a single person. Conventionally, since the catheter remains in the pinching hole it causes a deformation to gradually decrease the pinching power. However, the catheter according to this invention is, as compared with the conventional one, adapted to be pinched firmly only when necessary.

DETAILED DESCRIPTION OF THE INVENTION

Figure 1:
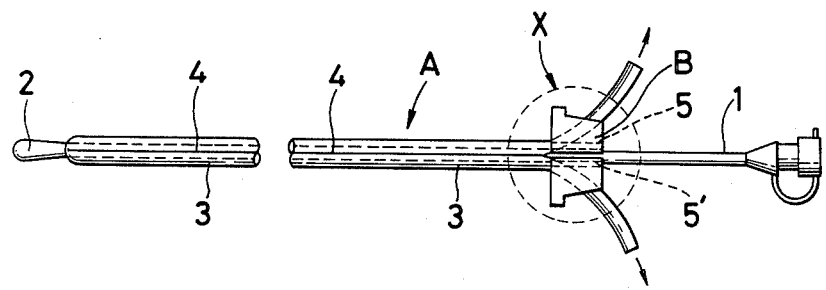
FIG. 1 is an explanatory view of a catheter for nasogastric intubation according to this invention.

The catheter for nasogastric intubation according to this invention will now be described by way of an embodiment shown in the accompanying drawings. FIG. 1 is an explanatory view of a catheter for nasogastric intubation in accordance with this invention, said catheter for nasogastric intubation comprising a nasogastric intubation tube A and a fixing means B. In the nasogastric intubation tube A, a very soft catheter body 1 is inserted and encased slidably into a plastic sheath tube 3 having slightly higher elasticity and rigidity than those of said catheter body. At the distal end portion of said catheter, a weight portion 2 is provided, while a side hole (not shown) for suppling a nutrition is provided slightly above the weight portion 2. The sheath tube 3 is adapted to be torn off by a longidutinal tear-off line 4 having a thin thickness over the full length thereof. The tear-off line 4 can be made by decreasing wall thickness of the sheath tube or forming with different material so as to be torn off.

Figure 2:
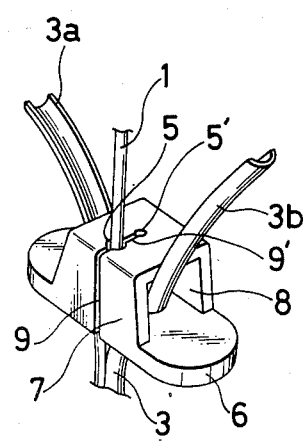
FIG. 2 and FIG. 3 are enlarged explanatory views showing X-portions of FIG. 1 respectively.
Figure 3:
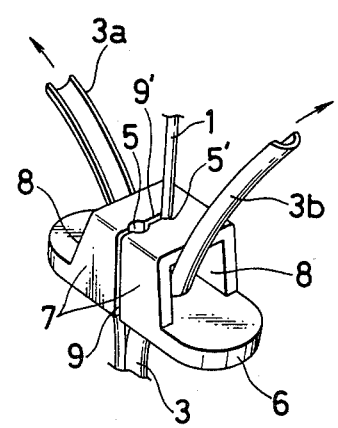

After the insertion of the tube A for nasogastric intubation having the catheter body 1 introduced therein, the tube A is fixed to a fixing means B externally of the nostril. FIG. 2 and FIG. 3 are enlarged explanatory views of X-portion in FIG. 1.

The fixing means B is integrally provided with a rising portion 7 on the base plate 6, and on both sides of this rising portion there are provided openings 8, 8 which can introduce the splitted sheath tubes 3a, 3b at the bottom of the base plate 6 in opposite directions to each other. At the side of the fixing means B making a right angle with these openings, there exists a side groove 9 into which the catheter body 1 is pushed from the side. At the inner part thereof, is a large hole 5 which can support the catheter body 1 loosely, and at the further inner part thereof, there is a small hole 5' which can pinch the catheter body 1 firmly, these two holes, large and small holes, 5, being in parallel and both and 5' are connected with a connecting groove 9' mutually.

In FIG. 2, the catheter body 1 is supported loosely in the larger hole 5, and when necessary, the catheter body 1 is caused to move into the small hole 5' through the connecting groove 9', to thereby firmly pinch it therein. This state is shown in the explanatory view of FIG. 3.

Figure 4:
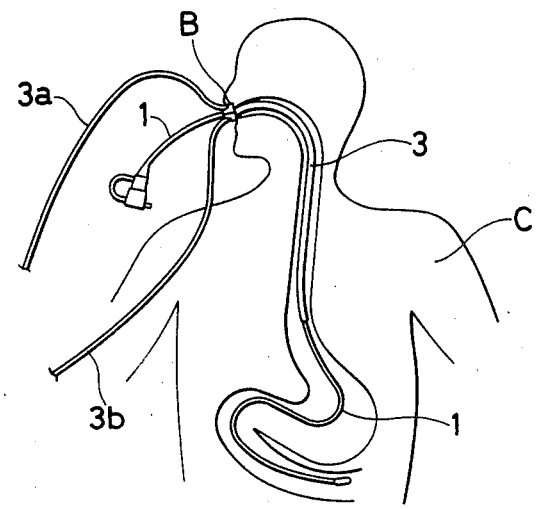
FIG. 4 is an explanatory view which shows an operation for inserting the catheter for nasogastric intubation according to this invention into the human body.

FIG. 4 is the explanatory view which shows the state where the catheter body 1 is set, while having been passed through the pylorus, and the sheath tube 3 is raised up from the openings 8, 8 of the fixing means B in opposite directions to each other through the fixing means B externally of the nostril as shown in FIG. 2, and wherein reference character C designates the human body. When all the sheath tube is raised up while being torn off, only the catheter body can remain held within the stomach.

Since this invention is constituted as described above, the catheter is slidably inserted into the sheath tube having the features described above over the full length thereof, thereby being able to practise the insertion of the catheter made of soft plastic tube to the nostril and the stomach with great ease and safety. Accordingly, the catheter of the invention is convenient as compared with a conventional catheter to greatly reduce pain to the patient and dangerousness.

Further, the catheter body with no weight portion can be inserted into the stomach by being inserted into this sheath tube. This is because the sheath tube has a proper elasticity and rigidity. Further even if the sheath tube is raised while being torn-off as described above, the catheter body is adapted not to be raised together with the sheath tube. There is such a method, for example, as forming the inner walls of the sheath tube or the surface of the catheter into sand-like surfaces to decrease the sliding resistance or using the lubricant. It will be also noted that two tear-off lines of the sheath tube are not always required, but even a single line can be used to achieve the intended object.

This sheath tube can be removed from the catheter body without using the fixing means B in such a manner that the distal end of the sheath tube is naturally moved upward by tearing it off by hands. In this case, however, two persons are required, one person firmly holding the catheter in position while the other performing the tearing-off work.

In accordance with this invention, the aforementioned fixing means B is used, and therefore, one person will suffice to effect this operation. Since the catheter body 1 is firmly pinched and fixed to the pinching groove 5 of the catheter pinching plate, the tearing-off operation can be performed by a single person, thus providing for an extreme convenience. Labor-saving effect may be brought forth by the inexpensive fixing means according to this invention.

Figure 5:
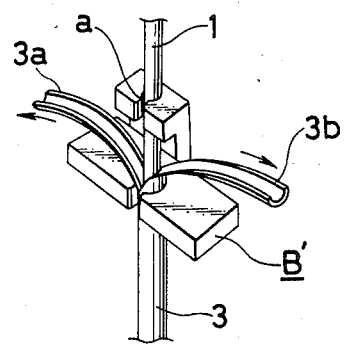
FIG. 5 is an explanatory view of a fixing means before improved.

A special feature of this invention is in its constitution wherein a large hole 5 and a small hole 5' which introduce the catheter body 1 therethrough are connected with a connecting groove 9'. A conventional fixing means B', for example, described in the patent application No. 79178/1984 by the same inventor shows in FIG. 5 that a hole a which inserts the catheter body 1 therein pinches the catheter firmly. Accordingly, if the catheter body 1 remains as it is for a while, it causes a deformation which contracts the pinching portion thereof, thereby reducing the pinching or holding power thereof, which causes other troubles. In view of those troubles, the catheter in accordance with this invention is held loosely by a large hole 5 and is moved to small hole 5' through the connecting groove 9' only when necessary (when the sheath tube is removed). Accordingly, there is no occurrence of the above mentioned defects. Further, although the fixing means B described in the specification of the above patent application No. 79178/1984 has such a defect as occurring a rotation when the sheath tube is divided into two parts, in the fixing means according to the present invention the rotation can be easily controlled and performed securely.

What is claimed is:

1. A catheter for nasogastric intubation of a patient comprising a catheter body, a plastic sheath tube, and a fixing means for said tube and catheter body adapted to be located at the nose of the patient for holding said catheter body, said tube having a longitudinal tear-off line over the full length thereof so that said tube is separable into longitudinal parts, said tube having an elasticity and a rigidity slightly larger than those of said catheter body, said catheter body being slidably insertable in said plastic sheath tube and together insertable into the patient, said fixing means comprising a base plate having opening means adapted to receive said sheath tube, said sheath tube being adapted to be pulled through said opening means and out of the patient and split along said tear-off line with said separable parts moving in opposite directions, said fixing means having a portion integrally connected to said base plate and having a relatively large passing hole adapted to softly hold the outer periphery of said catheter body and a relatively small passing hole adapted to firmly pinch said catheter body at a catheter pinch portion of said fixing means to hold it relative to the fixing means, said large passing hole and said small passing hole being communicated by a connecting groove, said catheter being movable sideway through said connecting groove and selectively between said large and small holes.

2. A catheter for nasogastric intubation of a patient comprising a catheter body, a sheath tube adapted to slidably receive said catheter body with said catheter body and sheath tube insertable together into the patient, said sheath tube being splitable and removable from said catheter body, and fixing means adapted to be located at the nose of the patient for holding said catheter body, said fixing means having a a wall portion with relatively large opening for receiving said catheter body and in which said catheter body is loosely held, said wall portion having a relatively small opening for receiving said catheter body in tight fitting engagement with sidewalls thereof so that said sheath tube is longitudinally movable relative to said catheter body during removal of said sheath tube from said catheter body, said catheter body being movable from either one of said openings to the other of said openings.

3. The catheter of claim 2 including passage means interconnecting said openings to allow lateral movement of said catheter body selectively from either of said openings to the other.

4. The catheter of claim 2 wherein said fixing means includes a second wall portion connected to said first named wall portion and having a third opening through which both said sheath tube and said catheter body are passable.

5. The catheter of claim 4 wherein said first named wall portion has a groove allowing lateral movement of said catheter into said first named wall portion, said relatively large and small openings being connected with said groove.

6. A catheter for nasogastric intubation of a patient comprising a catheter body, a sheath tube adapted to slidably receive said catheter body with said catheter body and sheath tube together being insertable into the patient, said sheath tube having a longitudinal tear-off line along which said sheath tube is splitable and removable from said catheter body, and fixing means adapted to be located at the nose of the patient for holding said catheter body, said fixing means including a first member having opening means through which said catheter body and sheath tube are passable, a second member connected to said first member and having a relatively large opening having sidewalls engagable with said catheter body for softly holding said catheter body, and a relatively small opening having sidewalls engagable with said catheter body in tight fitting engagement so that said sheath tube is longitudinally movable relative to said catheter when said catheter is in said small opening, said catheter body being laterally movable selectively from either one of said openings to the other of said openings.

7. The catheter of claim 6 wherein said first and second members of said fixing means are connected in generally parallel spaced relation.

8. The catheter of claim 6 wherein said second member of said fixing means has a groove interconnecting said openings and through which said catheter is movable sideways selectively into said openings.

9. The catheter of claim 6 wherein said fixing means has groove means allowing lateral movement of said catheter body into said fixing means and selectively into said relatively large and small openings.

10. A catheter of claim 9 wherein said second member has an upper wall and a pair of spaced sidewalls connecting said second member with said first member, said relatively large and small openings are in said upper walls, said groove means having groove portions in one of said sidewalls and said upper wall whereby said catheter body is movable laterally therein from the exterior of said fixing means and selectively into said relatively large and small openings.

11. The catheter of claim 10 wherein said sheath tube has a second longitudinal tear line along which said sheath tube is splitable so that said sheath tube is splitable into two longitudinally extending sections movable in different directions from the space between said first and second members.

12. Fixing means adapted to be positioned adjacent the nose of a patient for holding a nasal catheter and aiding in the removal of a splitable sheath surrounding the catheter comprising a first member having opening means therein sized to allow movement of the sheath therethrough, a second member connected to said first member and having a relatively large opening therethrough for receiving and loosely holding the catheter, a relatively small opening therethrough for receiving and holding the catheter in tight fitting relation against movement therethrough so that the sheath can be longitudinally moved relative to the catheter to facilitate removal thereof from the catheter, and a groove extending from the exterior surface of said second member into one of said openings to permit lateral movement of the catheter into the second member and one of said openings.

13. The fixing means of claim 12 wherein said second member has groove means interconnecting said openings to permit lateral movement of the catheter in said groove means and between said openings.

14. The fixing means of claim 13 further including a pair of spaced walls spacing said members apart, said groove portions thereof being in one of said sidewalls and in said first member.

* * * * *